United States Patent
Glickman et al.

(10) Patent No.: US 6,406,869 B1
(45) Date of Patent: *Jun. 18, 2002

(54) FLUORESCENT CAPTURE ASSAY FOR KINASE ACTIVITY EMPLOYING ANTI-PHOSPHOTYROSINE ANTIBODIES AS CAPTURE AND DETECTION AGENTS

(75) Inventors: J. Fraser Glickman, Garwood; James Inglese, Dayton, both of NJ (US); Bassam Damaj, San Diego, CA (US)

(73) Assignee: Pharmacopeia, Inc., Cranbury, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/425,549

(22) Filed: Oct. 22, 1999

(51) Int. Cl.[7] ............... G01N 33/543; G01N 33/53; G01N 33/574

(52) U.S. Cl. ............... 435/7.21; 435/4; 435/5; 435/6; 435/7; 435/7.23; 435/7.24; 435/7.4; 435/7.92; 435/7.94; 435/15; 435/21; 435/29; 435/188; 435/792; 436/518; 436/548; 436/547; 436/543; 424/8; 424/12; 23/230 B

(58) Field of Search ............... 435/7, 4, 5, 6, 435/7.21, 7.23, 7.24, 7.4, 7.94, 15, 21, 29, 188, 792; 424/8, 12; 436/518, 548, 547, 543; 23/230 B

(56) References Cited

U.S. PATENT DOCUMENTS

| | | | |
|---|---|---|---|
| 4,281,061 A | * | 7/1981 | Zuk et al. ............... 435/7 |
| 5,599,681 A | | 2/1997 | Epstein et al. ............... 435/7.23 |
| 5,616,726 A | | 4/1997 | Mitsuda et al. ............... 548/475 |
| 5,759,787 A | | 6/1998 | Strulovici ............... 435/7.4 |
| 5,763,198 A | * | 6/1998 | Hirth et al. ............... 435/7.21 |
| 5,958,719 A | | 9/1999 | Ullrich et al. ............... 435/21 |
| 6,066,462 A | | 5/2000 | Goueli ............... 435/7.1 |

FOREIGN PATENT DOCUMENTS

| | | | | |
|---|---|---|---|---|
| EP | 0 730 740 B1 | | 2/1998 | ......... G01N/33/573 |
| WO | WO 95/04136 | | 2/1995 | ............ C12N/9/12 |
| WO | WO-95/04136 A1 | * | 2/1995 | ............ C12N/9/12 |
| WO | WO-96/40276 A1 | * | 12/1996 | .......... A61K/49/00 |
| WO | WO-99/29894 A1 | * | 6/1999 | ............ C12Q/1/48 |

OTHER PUBLICATIONS

Cleaveland et al. "A Microtiter–Based Assay for the Detection of Protein Tyrosine Kinase Activity" *Analytical Biochemistry* 190, 249–253 (1990).

Giorgetti et al. "Insulin stimulates phosphatidylinositol–3–kinase activity in rat adipocytes" *Eur. J. Biochem.* 207, 599–606 (1992).

* cited by examiner

Primary Examiner—Christopher L. Chin
Assistant Examiner—Lisa V. Cook
(74) Attorney, Agent, or Firm—Heslin Rothenberg Farley & Mesiti P.C.

(57) ABSTRACT

A method for determining the level of tyrosine kinase activity in a biological sample is disclosed. The method employs an anti-phosphotyrosine antibody as both the capture agent and the detecting agent. The detecting antibody is labeled with a lanthanide ion, such as europium, as the signal generating entity. The method is particularly well suited to high throughput screening, for example, for compounds which modulate tyrosine kinase activity.

12 Claims, 2 Drawing Sheets

FLUORESCENT CAPTURE ASSAY FOR
KINASE ACTIVITY EMPLOYING
ANTI-PHOSPHOTYROSINE ANTIBODIES AS
CAPTURE AND DETECTION AGENTS

FIELD OF THE INVENTION

The present invention relates to a method for determining the level of kinase activity in a biological sample and, in particular, to a method of identifying drugs that inhibit tyrosine kinases, or drugs that inhibit receptors associated with tyrosine kinases.

BACKGROUND OF THE INVENTION

Protein phosphorylation is a common regulatory mechanism used by cells to selectively modify proteins carrying regulatory signals from outside the cell to the nucleus. The proteins that execute these biochemical modifications are a group of enzymes known as protein kinases. They may further be defined by the substrate residue that they target for phosphorylation. One group of protein kinases are the tyrosine kinases (TK's), which selectively phosphorylate a target protein on its tyrosine residues. Some tyrosine kinases are membrane-bound receptors and upon activation by a ligand, can autophosphorylate as well as modify substrates. The initiation of sequential phosphorylation by ligand stimulation is a paradigm that underlies the action of such effectors as, for example, epidermal growth factor (EGF), insulin, platelet-derived growth factor (PDGF), and fibroblast growth factor (FGF). The receptors for these ligands are tyrosine kinases and provide the interface between the binding of a ligand (hormone, growth factor) to the activation of one or more biochemical pathways. Ligand binding to a receptor tyrosine kinase activates its intrinsic enzymatic activity. Tyrosine kinases can also be cytoplasmic, non-receptor type enzymes and act as a downstream component of a signal transduction pathway.

The profound cellular effects mediated by tyrosine kinases, for example, their putative role in angiogenesis [Giroux, S. et al. Curr. Biol. 9: 369 (1999)] and lymphoid development [Nosaka, T., et al. Science 270: 800, (1995)] coupled with the implication that mutant or defective tyrosine kinase variants may be involved in tumorigenesis [Jeffers, M., et al. PNAS 94: 11445, (1997)], have made them attractive targets for the development of new therapeutic molecules.

Traditional methods for measuring the phosphorylation state of cellular proteins have relied on $^{32}$P-orthophosphate incorporation, for example, by exposing cells cultured in the presence of $^{32}$P-orthophosphate to the appropriate ligand or activator. Alternatively, phosphorylated tyrosine residues can be detected in immunoassays, for example, immunoprecipitation or blotting using a radiolabeled antiphosphotyrosine antibody. The fact that the techniques for detecting radioactive isotope (i.e. blotting, immunoprecipitation, gel electrophoresis) are very time consuming, however, minimizes the appeal of these methodologies for high throughput screening.

More recent methods utilize a standard enzyme-linked immunosorbent assay (ELISA) for measuring kinase activity. These methods utilize purified heterologous substrate protein or synthetic substrate peptides anchored to a microtiter plate. After exposure of the substrate molecule to a sample containing the appropriate kinase, the level of phosphorylation is evaluated with antiphosphotyrosine antibodies to quantitate the amount of phosphorylated protein bound to the plate. The obvious limitation of this type of assay is that the activity of a kinase specific for the particular substrate used, is the only activity detected. Additionally, methods such as protein tyrosine kinase enzyme assays are unable to eliminate as potential drug candidates, inhibitors which are not cell permeable and, therefore, are not good choices for therapeutic agents.

Hirth et al., U.S. Pat. No. 5,763,198, for example, describes an ELISA-type assay in which a substrate-specific antibody is used as an anchoring molecule to isolate a protein substrate from a cell lysate preparation and immobilize it on a solid phase support. Hirth's method then determines the level of kinase activity by evaluating the tyrosine phosphorylation state of the protein substrate bound to the solid phase using an anti-phosphotyrosine antibody as the detecting molecule. Other methods for measuring tyrosine kinase activity, particularly tyrosine kinase receptor activity, are described in WO95/04136, EP 0 730 740 B1, and U.S. Pat. No. 5,599,681.

The availability of an efficient, high throughput assay of kinase activity, particularly, one that is cell-based, is highly desirable because it provides the means, not only to characterize the phosphorylation status of a cell, but to identify agonists and antagonists useful as therapeutic agents for the treatment of a wide variety of human diseases.

SUMMARY OF THE INVENTION

Because the method of the present invention uses a capture agent capable of capturing any molecule containing a phosphorylated tyrosine, it can bind any tyrosine kinase substrate which has been phosphorylated. The method is, therefore, not limited to the measurement of a single tyrosine kinase. The method can be used with any kinase molecule without the necessity of having to use different capture agents for different kinases. Furthermore, the method of the present invention has the advantage of detecting cellular signaling events downstream of the receptor, thereby providing a means for detecting in a single test a drug's ability to inhibit more than one therapeutic target.

In one aspect, the invention relates to a method for measuring tyrosine kinase activity in a biological sample by contacting the sample with a solid phase coated with a first anti-phosphotyrosine antibody to capture phosphorylated proteins contained in the biological sample, and determining the amount of phosphorylated protein captured using a second labeled anti-phosphotyrosine antibody as the detecting molecule. The biological sample may be a purified homogeneous tyrosine kinase, a cell fraction, such as a cytosol or cell membrane preparation, cell or tissue extracts or bodily fluids, such as serum, plasma, urine or the like.

In another aspect, the invention relates to a method for measuring tyrosine kinase activity in a biological sample which employs a lanthanide ion as the reporter group on the labeled detecting antibody. By virtue of their unique fluorescence properties, use of lanthanide ions such as samarium (Sm), dysprosium (Dy), europium (Eu) and terbium (Tb) as labels make the method of the invention particularly well suited for highthroughput screening.

In yet another aspect, the invention features a method of screening for molecules, including agonist/antagonist small molecules, that modulate tyrosine kinase activity in whole cells, cell fractions, purified tyrosine kinase preparations or biological fluids. Samples are incubated with potential agonists or antagonists, and assayed for tyrosine kinase activity in accordance with the method described herein. Where the biological sample is a preparation of whole cells, the cells are fractionated, and the cytosol or cell membrane fractions are assayed for tyrosine kinase activity in accordance with the method of the present invention. The method can be used to evaluate cell activation through a general mechanism or through specific receptor activation by directly measuring the level of phosphorylated proteins within a biological sample that results from cell activation.

In yet another aspect, the invention relates to a kit for use in measuring the level of tyrosine kinase activity in a biological sample. The kit provides a solid support, for example a microtiter plate or beads, which is coated with an anti-phosphotyrosine antibody which captures phosphorylated proteins contained within the sample. A labeled anti-phosphotyrosine antibody is also provided to detect the amount of phosphorylated protein bound to the solid phase.

DETAILED DESCRIPTION OF THE INVENTION

Figure 1:
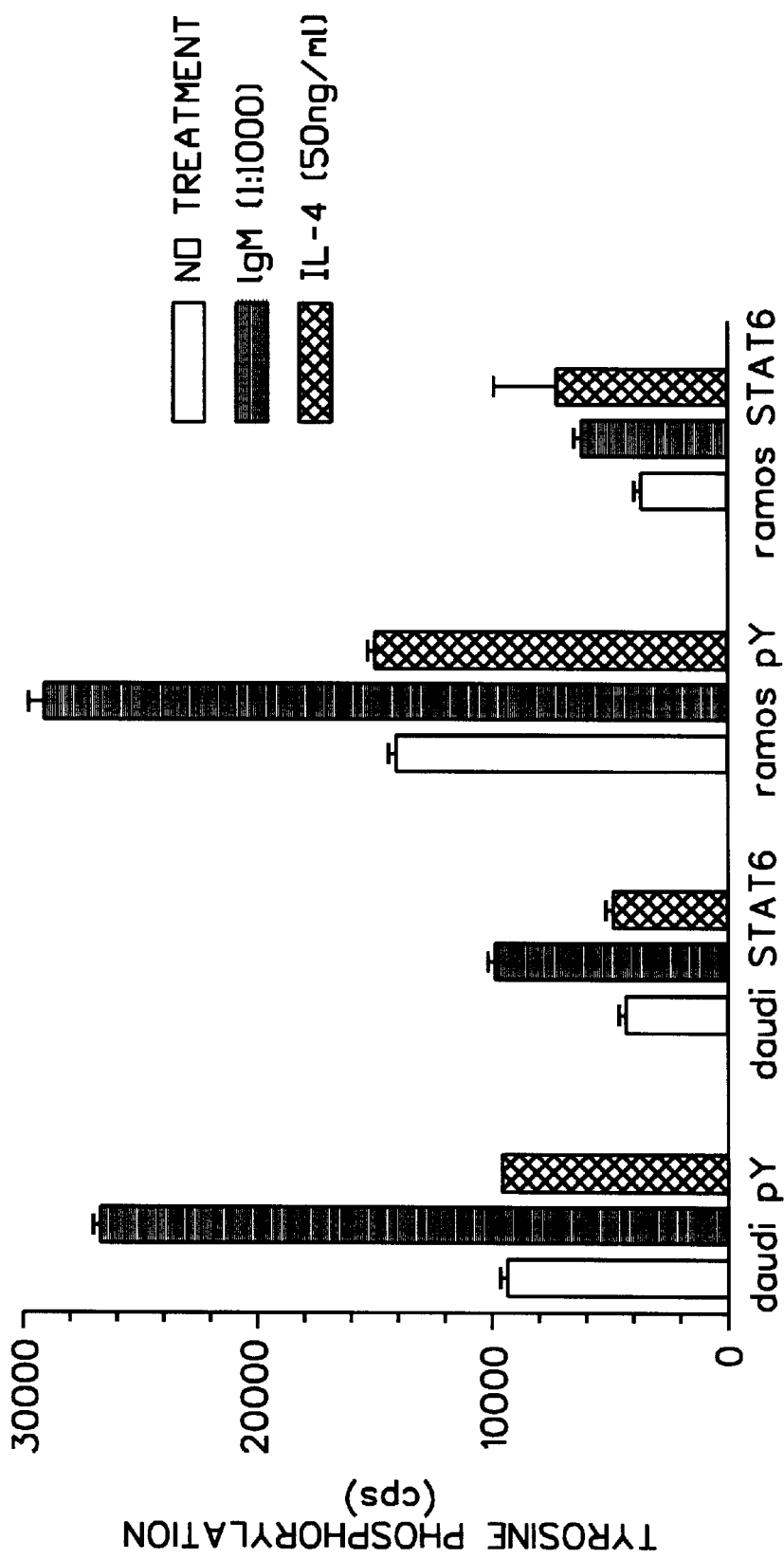
FIG. 1 shows the changes in tyrosine phosphorylation as detected by the method of the present invention when B-cells are stimulated with anti-IgM.

All patents, applications, publications, or other references that are listed herein are hereby incorporated by reference.

In the description that follows, certain conventions will be followed as regards the usage of terminology: The term "solid phase" refers to the solid support to which a capture agent, for example, an antibody, is attached and, in one embodiment, may be a microtiter plate. The method can be carried out in conventional 96-well microtiter plates, or in any other container or on any surface capable of holding liquid samples and of being scanned by the appropriate detection device, for example a plate reader or microscope. Other examples include 6 to 1536-well plates, and microscope slides.

In another embodiment, a suspendable solid phase can be employed, including cellulose beads, controlled pore-glass beads, silica gels, poly-acrylamide beads, latex beads, dimethylacrylamide beads, glass particles coated with hydrophobic polymers and other types of polystyrene beads. The preferred bead size is less than about 50 µm in diameter, most preferably less than 10 µm but greater than 1 µm. A preferred suspendable support is a 6.2 µm bead made of polystyrene and commercially available from Spherotech (Libertyville, Ill.). Such beads are avidin coated or coated with protein A, typically containing $10^6$ binding sites per bead.

The term "capture agent" refers to a compound or agent which is able to adhere to a solid phase and which is selective for phosphorylated proteins contained in the biological sample to be assayed and typically is an affinity-purified polyclonal antibody or a monoclonal antibody. Solid phases used for the immobilization of phosphorylated molecules may be prepared by coating with the capture agent (anti-phosphotyrosine), either directly or indirectly. Methods for immobilizing antibodies are known in the art and are described in Harlow, E. and D. Lane, *Antibodies: A Laboratory Manual,* (1988) Cold Spring Harbor Laboratory, Cold Spring Harbor, New York which is incorporated herein by reference. In one embodiment, the anti-phosphotyrosine antibody is immobilized to the solid phase by an antibody bound to the solid phase which is specific for the Fc portion of the anti-phosphotyrosine antibody. In another embodiment, the anti-phosphotyrosine antibody is adsorbed directly to the solid phase.

The term "biological sample" refers to any source of protein tyrosine kinase activity and is intended to encompass purified kinase preparations, cells, both whole and fractionated, cell and tissue extracts, and bodily fluids, for example, urine, serum, plasma and the like.

Sandwich assays are among the most useful and commonly used assays and are particularly useful in the present invention. A number of variations of the sandwich assay technique exist. In a typical assay, an antibody is brought into contact with a biological sample containing one or more proteins of interest. After a suitable period of incubation, for a period of time sufficient to allow formation of an antibody-protein complex, a second antibody with specificity for a second distinct epitope on the molecule bound by the first, labelled with a reporter molecule capable of producing a detectable signal, is then added and incubated allowing sufficient time for the formation of a tertiary complex. Any unreacted material is washed away, and the presence of the second antibody bound is determined by observation of the visible signal, and may be quantitated by comparing with a control sample containing known amounts of hapten. Variations on the assay include using a first antibody labelled with a reporter molecule. In addition, the "capture" antibodies may be immobilized on a solid support.

Typically, the capture agent and the detecting agent are different molecules each having specificity for different regions of the molecule to be captured. Capture agents are usually chosen so that binding of the capture agent does not sterically block access to the phosphorylated tyrosines of the molecule of interest. It has now been unexpectedly found that an anti-phosphotyrosine antibody can be used as the capture agent and as the detection agent in the same assay. The method of the instant invention employs a standard ELISA-like sandwich assay. Unlike other similar assays, however, its versatility stems from its use of an anti-phosphotyrosine antibody as both the capture agent and the detection agent. By doing so, the method is able to capture any tyrosine-containing protein in the biological sample which is phosphorylated, thereby providing a mechanism to evaluate phosphorylation that results from cell activation.

Activation of a cell most frequently occurs when an appropriate ligand binds to its receptor on the cell surface. Such ligands may include growth and differentiation factors such as epidermal growth factor (EGF); platelet-derived growth factor (PDGF); chemokines, such as the interleukins; SDF-1 and GM-CSF (activates JAK2 in a variety of cells). Cells can also be activated by mitogen stimulation, for example, concanavalin A or phytohemagglutanin for T-cells, pokeweed mitogen or lipopolysaccharide for B-cells; or an antibody to a cell surface marker, such as IgM.

Because they focus on a specific substrate, current methodologies are only able to detect phosphorylation by a particular kinase. The method of the present invention confers an advantage in that it utilizes a capture agent which can capture any protein in the biological sample such as a cell lysate which has a tyrosine residue that is phosphorylated. Because detection is not limited to a single kinase, a broader perspective of the overall phosphorylation resulting from an activation event can be obtained. Furthermore, identification of inhibitors which down-regulate ligand-induced phosphorylation is possible.

In a preferred embodiment, method of detection for the subject method is time resolved fluorescence and the detecting agent, anti-phosphotyrosine antibody, is labeled with a lanthanide ion, preferably, Europium. Lanthanide ions have unique fluorescence properties which make them particularly well suited for high throughput assays such as the method described herein. While samarium (Sm) and dysprosium (Dy) are suitable for use in the instant method, europium (Eu) and terbium (Tb) are preferred, with europium being most preferred.

In accordance with the method of the present invention, a solid support, for example, a 96-well polystyrene microtiter plate is coated with an anti-phosphotyrosine antibody, for example, pY99 (Santa Cruz Biotech, Inc., Santa Cruz, Calif.), by preparing a solution having an antibody concentration in the range of 0.01 μg/ml to 25 μg/ml, with a preferred concentration of 2.5 μg/ml, in Tris buffered saline (TBS) having a pH in the range of 7.5–8.5 and adding an aliquot of antibody solution to each well of the plate. A variety of anti-phosphotyrosine antibodies, available commercially from a number of sources, are suitable for the method of the present invention. For example, PY-7E1, PY-1B2, and PY20 are monoclonal mouse anti-phosphotyrosine antibodies available from Zymed (San Francisco, Calif.) individually or as a cocktail sold under the trademark PY-PLUS™. Zymed also offers an affinity-purified polyclonal rabbit anti-phosphotyrosine antibody, Z-PY1. A mouse anti-phosphotyrosine antibody, clone PT-66 is available from Sigma (St. Louis, Mo.). Furthermore, polyclonal phosphotyrosine antibodies may be raised in a variety of species according to immunization methods well known in the art. A method for the production of monoclonal phosphotyrosine antibodies is described in U.S. Pat. No. 4,543,439, the contents of which are hereby incorporated by reference.

The plate is then incubated for a period of time sufficient to allow adsorption of the antibody to the plate. Plates coated in this manner are then rinsed to remove excess antibody and a blocking solution, for example, that sold under the trademark, SUPERBLOCK™ (Pierce Chemical, Rockford, Ill.) is added followed by an incubation period sufficient to allow any regions of the plate not coated with antibody to be coated with the blocking agent. Other suitable blocking agents include proteins that do not cross-react with any of the reagents in the assay, for example, bovine serum albumin (BSA), gelatin, casein or milk protein. At this point, the plates may be stored at 4° C. for up to two weeks.

An aliquot of the biological sample to be evaluated is added to the capture assay plate. Where the biological sample is a preparation of whole cells, prior to assay, the cells to be evaluated are lysed with 50 μl of a standard detergent buffer containing phosphatase inhibitors, for example, 10% triton X-100, 50 mM sodium fluoride, 2 mM EDTA, 2 mM EGTA. The plate containing the cell lysates is frozen at −80° C. and may be stored indefinitely. To assay the cell lysates for kinase activity, the plate is thawed at 37° C., and 100 μl of tris buffered saline with 0.1% tween 20 is added to each well. After shaking the plate for 15 minutes, 180 μl of the cell lysate from each well is transferred to the capture assay plate described above.

After addition of the sample, the assay plate is incubated at room temperature with shaking for a period of time sufficient to allow the phosphorylated proteins contained in the sample to bind to the antibody coated plate, for example, anywhere from 15 minutes to several hours. The plate is then washed to remove unbound protein. Relative phosphorylated protein levels are detected using a lanthanide-chelate labeled anti-phosphotyrosine antibody in tris buffered saline (pH 8.0). An anti-phosphotyrosine antibody which is different from or the same as the one used for the capture antibody may be labelled for use as the detecting molecule. Any of the anti-phosphotyrosine antibodies described above for use as the capture agent are suitable for use as the detecting antibody as well. Polyclonal as well as monoclonal antibodies may be labelled with a lanthanide ion.

The method of the present invention, employs a lanthanide-chelate as the label for the detecting antibody. The long-lived and sharp emission spectrum of certain lanthanide ions has allowed antibody labeling with detection sensitivities similar to those obtainable with radioisotopes. Use of europium and terbium chelators for time-resolved fluorometric assays is described in U.S. Pat. No. 5,854,008, the contents of which are hereby incorporated by reference. In a preferred embodiment, an antibody-$Eu^{+3}$ conjugate is formed in accordance with manufacturer's instructions. Approximately 100 μl of labeled antibody is added to each well and the plate is permitted to incubate with shaking for a period of time sufficient to allow binding of the antibody to the phosphorylated protein bound to the plate. The plate is then washed to remove unbound antibody. Enhancement Solution for measuring $Eu^{3+}$ (E. G. & G. Wallac, Turku, FI) is added and the amount of labeled antibody bound is measured using a time-resolved fluorescence plate reader (Wallac Oy, Turku, FI).

Screening Test Compounds

The method of the present invention can be used to test for compounds that modulate tyrosine kinase activity and which act as tyrosine kinase receptor function agonists or antagonists. In one embodiment, cells bearing the receptor of interest are exposed to known agonists, known antagonists, and/or test compounds which may be, or may contain, agonists or antagonists. An agonist, antagonist, or test compound may be a chemical compound, a mixture of chemical compounds, a biological macromolecule, or an extract made from biological materials such as bacteria, plants, fungi, or animal cells or tissues. Test compounds are evaluated for potential activity as agonists or antagonists of receptor activation by inclusion in screening assays described herein. An "agonist" enhances the activity of a receptor; an "antagonist" diminishes the activity of a receptor. The terms "agonist" and "antagonist", as used herein, do not imply a particular mechanism of function.

In accordance with the method of the present invention, cells are incubated with a known agonist, a test compound, or a combination of the two for a period of time in the range of 1 minute to several hours and a range of temperature from about 4° C. to about 37° C. In a preferred embodiment, the cells are incubated in the presence of test compound and ligand/activator for 15 minutes at room temperature. The cells are then lysed and a sample of the cell lysate assayed in a capture assay plate as described above.

In a preferred embodiment, the resulting cell lysate is transferred to a well of a microtiter plate to which an antibody against the phosphorylated proteins is immobilized. In an alternative embodiment, a cell membrane fraction, especially a plasma membrane fraction can be purified from the cells treated with a test compound, using standard methods (Methods in Enzymology Vol. 198) and assayed for tyrosine kinase activity in accordance with the method of the subject invention.

Time Resolved Fluorescence

In one embodiment, the detection method employed for determining the level of anti-phosphotyrosine detecting antibody is time-resolved fluorescence (TRF). Lanthanide-ion-chelates possess unique fluorescent properties, making them particularly good reporter groups for high-throughput applications. For this method, anti-phosphotyrosine antibodies may be labelled with europium (Eu), terbium (Tb), dysprosium (Dy) or samarium (Sm), with europium and terbium being preferred and europium being most preferred. In a preferred embodiment, anti-phosphotyrosine antibodies, for example, pY99 (available from Santa Cruz Biotech, Inc., Santa Cruz, Calif.; Upstate Biotechnology, Inc., Lake Placid, N.Y.; or Transduction Laboratories,) are labeled with a lanthanide ion, such as Europium ($Eu^{3+}$) according to manufacturer's instructions. Briefly, anti-phosphotyrosine antibody (1 mg) is dialyzed against 50 mM sodium bicarbonate pH8.35, 0.9% NaCl and adjusted to a concentration of 2 mg/ml. 0.5 ml of the antibody solution is mixed with 300 nmol Europium-DTTA labeling reagent (E. G. & G. Wallac, Inc., Turku, FI) in bicarbonate buffer (50 mM Sodium Bicarbonate, 150 mM NaCl, pH 8.0) and the reaction mixture is incubated at 16° C. overnight in the dark. $Eu^{3+}$-chelate-labeled antibody is then separated from free $Eu^{3+}$-chelate by gel-filtration chromatography on an S200 FPLC column (Pharmacia, Bridgewater, N.J.).

EXAMPLE 1

The following example(s) describes the application of the assay of the invention using cells expressing T-cell receptor (T-cells) or IgM (B-cells).

According to the method of the present invention, cells of interest were grown under conditions appropriate for growth, proliferation and for expression of the receptor of interest according to methods of cell culture known to one of ordinary skill in the art.

96-well polystyrene plates were coated with an anti-phosphotyrosine antibody, pY99 (Santa Cruz Biotech, Inc., Santa Cruz, Calif.), by adding 200 μl of an antibody solution in Tris buffered saline (TBS) pH 8.0 at a concentration of 2.5 μg/ml. The plates were incubated for three hours at room temperature. The plates were then rinsed and 300 μl of blocking solution, sold under the trademark, SUPER-BLOCK™ (Pierce Chemical, Rockford, Ill.) was added and the plates were incubated for two hours. At this point, the plates may be stored at 4° C. for up to two weeks.

50 μl of a cell suspension containing human or animal cells of interest, for example, Jurkat T cells, Ramos B cells, or Daudi B cells, at a cell density of $2-5 \times 10^5$, were added to each well of a 96-well polypropylene U-bottom plate. 10 μl of test compound in a physiologic buffer was added to the cells to a final concentration in the range of 1–10 μM. Control wells received 10 μl of buffer with no test compound. The appropriate ligand or activator for the receptor of interest, for example, anti-CD3 antibody to activate the T-cell receptor, or anti-IgM to activate the B-cells via cell surface immunoglobulin, was added in 10 μl, so that the final concentration of ligand was 100 ng/ml; the plate was incubated for 15 minutes. The cells were then lysed with 50 μl of standard detergent buffer containing phosphatase inhibitors (10% triton X-100, 50 mM sodium fluoride, 2 mM EDTA, 2 mM EGTA). The plate was frozen at −80° C. and may be stored indefinitely.

To assay the cell lysates for kinase activity, the plate was thawed at 37° C., and 100 μl of tris buffered saline with 0.1% Tween 20 was added to each well. After shaking the plate for 15 minutes, 180 μl of the cell lysate from each well was transferred to the capture plate described above. The capture plate was incubated for one hour at room temperature with shaking to allow the phosphorylated proteins contained in the cell lysate to bind to the antibody coated plate. The plate was then washed to remove unbound protein. Relative phosphorylated protein levels were detected by adding 100 μl of a 0.2 μg/ml solution of europium-chelate labeled anti-phosphotyrosine antibody in tris buffered saline (pH 8.0) to each well and allowing the plate to incubate for one hour with shaking. The plate was then washed to remove unbound antibody. Enhancement Solution for measuring $Eu^{3+}$ (E. G. & G. Wallac, Turku, FI) was added and the amount of labeled antibody bound was measured using a time-resolved fluorescence plate reader, for example, a Wallac 1420, or Victor MLC (Wallac Oy, Turku, FI).

The results, as shown in FIG. 1, indicate that changes in tyrosine phosphorylation can be detected by stimulating Daudi or Ramos B-cells with anti-IgM but not significantly with IL-4. It is known that an anti-IgM antibody, which stimulates the B-cell receptor, results in detectable changes in phosphorylation of many proteins.

EXAMPLE 2

Figure 2:
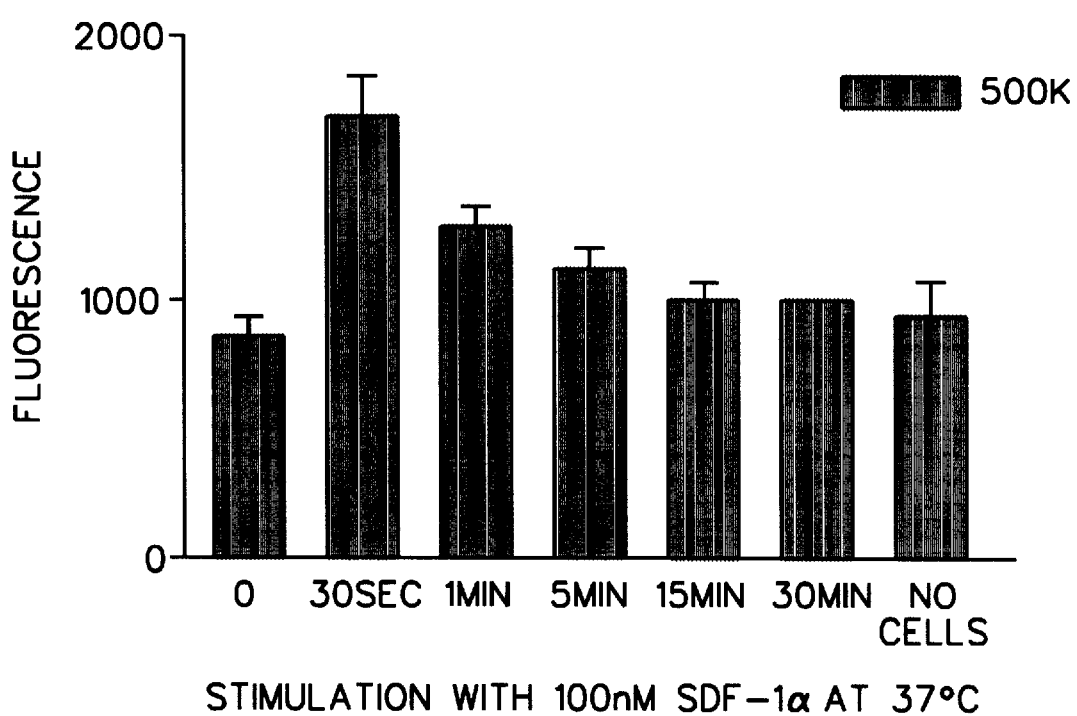
FIG. 2 shows the results of stimulating Jurkat cells with SDF-1α for various lengths of time prior to assaying for tyrosine kinase activity in accordance with the method of the invention.

In this example, Jurkat cells were incubated at 37° C. with 100 nM SDF-1α for various time intervals prior to harvesting of the cells and measurement of tyrosine kinase activity. The results are shown in FIG. 2. There is a decrease in kinase activity (as indicated by a decrease in fluorescence) as time increases suggesting an intracellular dephosphorylation event following cell activation by SDF-1α.

What is claimed is:

1. A method for measuring protein tyrosine kinase activity in a biological sample, said method comprising the steps:

(a) coating a solid phase with a first anti-phosphotyrosine antibody;

(b) contacting a biological sample with said solid phase coated with said first anti-phosphotyrosine antibody so that phosphorylated tyrosine-containing molecules in the biological sample are bound by the antibody to the solid phase;

(c) contacting bound phosphorylated tyrosine-containing molecules with a second anti-phosphotyrosine antibody;

(d) removing unbound second anti-phosphotyrosine antibody; and (e) determining the level of tyrosine kinase activity in said biological sample by measuring the amount of said second anti-phosphotyrosine.

2. The method of claim 1, wherein said second anti-phosphotyrosine antibody is labeled.

3. The method of claim 1, wherein said first and second anti-phosphotyrosine antibodies are the same.

4. The method of claim 2, wherein the label on said labeled second anti-phosphotyrosine antibody is a lanthanide ion.

5. The method of claim 4, wherein said lanthanide ion is europium.

6. The method of claim 1 wherein said biological sample is a cell fraction.

7. The method of claim 1 wherein said biological sample is a lysate of whole cells.

8. The method of claim 1 wherein said biological sample is a purified homogeneous tyrosine kinase.

9. The method of claim 1 wherein said solid phase is a microtiter plate.

10. The method of claim 1 wherein said solid phase is a bead.

11. A kit for use in measuring the level of tyrosine kinase activity in a biological sample comprising:

(a) a solid phase coated with a first anti-phosphotyrosine antibody;

(b) a second anti-phosphotyrosine antibody, wherein said second anti-phosphotyrosine antibody is labeled with a lanthanide ion; and (c) instructions for carrying out a method for using said kit.

12. The kit of claim 11 wherein said lanthanide ion is europium.

* * * * *

UNITED STATES PATENT AND TRADEMARK OFFICE
CERTIFICATE OF CORRECTION

PATENT NO.    : 6,406,869 B1
DATED         : June 18, 2002
INVENTOR(S)   : Glickman et al.

It is certified that error appears in the above-identified patent and that said Letters Patent is hereby corrected as shown below:

<u>Column 8,</u>
Line 36, insert the word -- antibody -- at the end of the sentence Signed and Sealed this Fifteenth Day of October, 2002

*Attest:*

*Attesting Officer*

JAMES E. ROGAN
*Director of the United States Patent and Trademark Office*